United States Patent
Roncalez et al.

(10) Patent No.: US 10,524,739 B2
(45) Date of Patent: Jan. 7, 2020

(54) TWIN-MONITOR ELECTRONIC DISPLAY SYSTEM

(71) Applicant: Super Sonic Imagine, Aixen en Provence (FR)

(72) Inventors: Pascal Roncalez, Eguilles (FR); Pierre-Lin Laneyrie, Aix en Provence (FR)

(73) Assignee: Super Sonic Imagine, Aix en Provence (FR)

( * ) Notice: Subject to any disclaimer, the term of this patent is extended or adjusted under 35 U.S.C. 154(b) by 635 days.

(21) Appl. No.: 14/166,088

(22) Filed: Jan. 28, 2014

(65) Prior Publication Data

US 2014/0143690 A1 May 22, 2014
US 2015/0150521 A2 Jun. 4, 2015

Related U.S. Application Data

(63) Continuation of application No. 12/920,070, filed as application No. PCT/EP2009/052520 on Mar. 3, 2009, now Pat. No. 8,659,507.

(Continued)

(30) Foreign Application Priority Data

Mar. 4, 2008 (FR) ...................................... 08 51397

(51) Int. Cl.
*A61B 5/00* (2006.01)
*G06F 3/0488* (2013.01)
(Continued)

(52) U.S. Cl.
CPC ............ *A61B 5/7445* (2013.01); *A61B 8/464* (2013.01); *A61B 8/467* (2013.01); *A61B 8/468* (2013.01);
(Continued)

(58) Field of Classification Search
CPC ....... A61B 5/7445; A61B 8/468; A61B 8/467; A61B 8/464; A61B 8/469; A61B 5/1118;
(Continued)

(56) References Cited

U.S. PATENT DOCUMENTS 5,250,929 A 10/1993 Hoffman et al.
6,468,212 B1 10/2002 Scott et al.
(Continued)

FOREIGN PATENT DOCUMENTS

DE 19739284 3/1999
JP 09-173333 7/1997
(Continued)

OTHER PUBLICATIONS

Office Action for related Korean Patent Application No. 2015-7013069 dated Jun. 15, 2015.
(Continued)

*Primary Examiner* — Calvin C Ma
(74) *Attorney, Agent, or Firm* — Caesar Rivise, PC (57) ABSTRACT

The invention concerns an electronic display system, associated with ultrasound imaging equipment capable of for capturing a medium image, said system comprising a first monitor to display an ultrasound image captured by the ultrasound imaging equipment and image processing means. The system comprises a second touch-screen monitor, means to duplicate the ultrasound image, means to send this duplicate to the second monitor on which at least part thereof is displayed, means to display at least one graphical element which, by means screen tactility, is used to perform at least one processing operation on the ultrasound image, means for instant application of all processing operations performed using the second monitor to the duplicate ultrasound image displayed on the second monitor, and means for instant or deferred application to the ultrasound image displayed on
(Continued)

the first monitor of the processing operations performed on the duplicate ultrasound image via the second monitor.

21 Claims, 3 Drawing Sheets

Related U.S. Application Data (60) Provisional application No. 61/151,240, filed on Feb. 10, 2009.

(51) Int. Cl.
| | | |
|---|---|---|
| *G06F 3/14* | (2006.01) | |
| *G06T 7/00* | (2017.01) | |
| *G06F 3/0484* | (2013.01) | |
| *A61B 8/00* | (2006.01) | |
| *G06F 3/0481* | (2013.01) | |

(52) U.S. Cl.
CPC ........ *G06F 3/0488* (2013.01); *G06F 3/04812* (2013.01); *G06F 3/04842* (2013.01); *G06F 3/04847* (2013.01); *G06F 3/04883* (2013.01); *G06F 3/1423* (2013.01); *G06T 7/0012* (2013.01); *A61B 8/469* (2013.01); *G06T 2200/24* (2013.01); *G06T 2207/10132* (2013.01); *G06T 2207/30004* (2013.01); *G09G 2340/12* (2013.01)

(58) Field of Classification Search
CPC ............. G06F 3/04812; G06F 3/04842; G06F 3/04847; G06F 3/0488; G06F 3/04883; G06F 3/1423; G06T 7/0012; G06T 2207/30004; G06T 2207/10132; G06T 2200/24; G09G 2340/12
USPC .......................................... 345/3.1, 173, 174
See application file for complete search history.

(56) References Cited

U.S. PATENT DOCUMENTS

| | | | | |
|---|---|---|---|---|
| 8,593,419 | B2* | 11/2013 | Thorn ................. | G06F 3/04883 345/173 |
| 2002/0005108 | A1* | 1/2002 | Ludwig ................... | G10H 1/00 84/600 |
| 2002/0085668 | A1* | 7/2002 | Blumhofer ............. | A61B 6/547 378/68 |
| 2003/0105400 | A1 | 6/2003 | Yawata et al. | |
| 2004/0150963 | A1 | 8/2004 | Holmberg et al. | |
| 2005/0059892 | A1 | 3/2005 | Dubois et al. | |
| 2006/0074287 | A1 | 4/2006 | Neumann et al. | |
| 2006/0173308 | A1 | 8/2006 | Sasaki | |
| 2006/0238625 | A1* | 10/2006 | Sasaki ................ | H04N 1/00416 348/231.3 |
| 2007/0016029 | A1 | 1/2007 | Donaldson et al. | |
| 2007/0230758 | A1* | 10/2007 | Fan ............................ | G06T 7/32 382/128 |
| 2007/0294634 | A1* | 12/2007 | Kokemohr .......... | G06F 3/04845 715/781 |
| 2008/0119731 | A1 | 5/2008 | Becerra et al. | |
| 2009/0043195 | A1* | 2/2009 | Poland ..................... | A61B 8/00 600/437 |
| 2009/0163814 | A1* | 6/2009 | Amemiya ................ | A61B 8/08 600/443 |
| 2009/0213141 | A1 | 8/2009 | Gao | |
| 2009/0306514 | A1* | 12/2009 | Imamura .................. | A61B 8/14 600/458 |
| 2011/0182137 | A1* | 7/2011 | Ozaki ...................... | A61B 8/00 367/7 |

FOREIGN PATENT DOCUMENTS

| | | |
|---|---|---|
| JP | 10-248843 | 9/1998 |
| JP | 11-318906 | 11/1999 |
| JP | 2000-316864 | 11/2000 |
| JP | 2002-248099 | 9/2002 |
| JP | 2004033658 | 2/2004 |
| JP | 2005-245961 | 9/2005 |
| JP | 2006513731 A | 4/2006 |
| JP | 2008141508 | 6/2006 |
| JP | 2007-873324 | 4/2007 |
| JP | 2007202829 | 8/2007 |
| JP | 2007260188 | 10/2007 |
| JP | 2008-515519 | 5/2008 |
| JP | 5208010 B2 | 6/2013 |
| WO | WO 99/13396 | 3/1999 |
| WO | WO 00/31678 | 6/2000 |
| WO | WO 03/098523 | 11/2003 |
| WO | WO 2006/035398 | 4/2006 |
| WO | WO 2006/038182 | 4/2006 |
| WO | 2006126131 A1 | 11/2006 |

OTHER PUBLICATIONS

Office Action for related Japanese Patent Application No. 2010-549131 dated Aug. 4, 2015.
International Search Report for related PCT Application No. PCT/EP2009/052520 dated Jun. 16, 2009.
Office Action for corresponding Japanese Patent Application No. JP2014-130249 dated Mar. 31, 2015.
English language abstract for JP 5208010 B2 (2013).
English language translation of Office Action from corresponding JP 2010-549131 dated Aug. 4, 2015.

* cited by examiner

TWIN-MONITOR ELECTRONIC DISPLAY SYSTEM

CROSS-REFERENCE TO RELATED APPLICATIONS

This is a continuation application and takes the benefit under 35 U.S.C. § 120 of application Ser. No. 12/920,070 (now U.S. Pat. No. 8,659,507) filed on Aug. 27, 2010 which is a national stage application that claims the benefit under 35 U.S.C. § 371 of International Application No. PCT/EP2009/052520 filed on Mar. 3, 2009, all of which are entitled TWIN-MONITOR ELECTRONIC DISPLAY SYSTEM, which in turn takes its priority from French Application No. 0851397 filed on Mar. 4, 2008 and U.S. Provisional Application No. 61/151,240 filed on Feb. 10, 2009, and all of whose entire disclosures are incorporated by reference herein.

BACKGROUND OF THE INVENTION

The present invention relates to the general area of electronic systems for displaying images in general, and more particularly to those intended to be coupled with ultrasound imaging equipment capable of capturing an image of a medium.

In general, such electronic display systems comprise a monitor to display the ultrasound image such as captured by the ultrasound imaging equipment. These electronic display systems comprise image processing means, or are connected to processing means.

Such electronic display systems are known to persons skilled in the art, for example through documents U.S. Pat. Nos. 6,063,030, 6,468,212 and 7,022,075.

These patent documents describe display systems comprising a single viewing monitor. This single monitor defines a display space which is shared by the ultrasound image and by the graphical elements used to perform processing of the ultrasound image.

The major drawback with these electronic display systems is that it is necessary to reduce the size of the ultrasound image displayed in full-screen format, either by changing the scale of or by cropping the image, so that it is possible to display the graphical elements used to perform processing of the displayed ultrasound image.

It is therefore not possible to maintain the entirety of the displayed image or to maintain maximum resolution for this image.

Yet, in the area of ultrasound imaging, it has come to be considered as being particularly helpful to have the entirety of the image displayed with the best acquired resolution in order to detect any biological anomalies and/or to identify position relative to the entirety of the image such as taken.

This is why numerous systems also offer the use of a touch-screen monitor used solely to conduct image processing, but whose effect can only be seen on the main display monitor. This effectively guarantees good image quality, but compels the user to give attention simultaneously to two monitors, which in the setting of a medical examination is hardly feasible or acceptable.

More broadly, in this area, it is also desirable to achieve maximum simplification of the user interface for ultrasound image display and processing systems. The ultrasound equipment and its display system are generally operated by medical staff that appreciate user-friendly tools with fast and easy access.

SUMMARY OF THE INVENTION

The present invention therefore chiefly sets out to overcome the disadvantages of prior art electronic display systems by proposing an electronic display system intended to be coupled with ultrasound imaging apparatus able to capture an image of a medium, said system comprising a first monitor to display an ultrasound image such as captured using the ultrasound imaging apparatus, and image processing means, characterized in that it further comprises at least:
  a second, touch-screen, monitor,
    means to duplicate the ultrasound image, capable of generating a duplicate of the ultrasound image displayed on the first monitor, means to send this duplicate to the second monitor in which at least part thereof is then displayed,
    means to display, on the second monitor, at least one graphical element used to perform at least one processing operation of the ultrasound image, using the tactility of the screen, these means to display the graphical element being such that the graphical element is displayed superimposed over the duplicate ultrasound image,
  means for instantaneous application of all the processing operations performed, using the second monitor, onto the duplicate ultrasound image displayed on the second monitor, and
  means for instantaneous or deferred application, onto the ultrasound image displayed on the first monitor, of all or part of the processing operations performed, while using the second monitor, on the duplicate ultrasound image.

With such a display system, display of the ultrasound image such as acquired can be guaranteed with maximum definition and maximum size on the first monitor, together with the display of the image adapted for processing the acquired image in lower definition and/or reduced size.

The combination of the duplicate ultrasound image with the presence of graphical elements to perform processing on the second monitor provides very simple, user-friendly access to the image processing controls. The second monitor is indeed specifically dedicated to these controls whilst offering display of the ultrasound image such as acquired in the form of a duplicate thereof, in a smaller format on this second monitor.

Processing controls and monitoring are therefore facilitated by the invention since processing operations are applied instantly to the duplicate of the ultrasound image such as displayed on the second monitor before they are sent to the first monitor either immediately or in deferred manner.

By displaying the graphical element, according to the invention, for the performing of the processing operation or operations, it becomes particularly easy to monitor the changes induced by the processing performed on the duplicate image. This further makes it possible to avoid having to make any penalizing reduction in the size of the duplicate ultrasound image.

According to one particular characteristic of the invention, the application means allow a choice to be made between immediate or deferred application of the processing made.

According to another particular characteristic of the invention, the application means allow to select which processing operations are to be applied to the ultrasound image from among those performed on the duplicate ultrasound image by means of the second monitor.

The last two characteristics provide the user with manual control over the processing operations that are wished to be applied to the ultrasound image displayed on the first monitor, hence to the image of best quality and greatest size.

When transferring the results of processing operations to the ultrasound image displayed on the first monitor, it is advantageous to have the ability only to apply part of the processing operations that was applied to the second monitor, and hence to choose which processing operations to apply.

Therefore the user may, in particular, wish to apply one processing element solely to one particular part of the image which is previously selected and displayed on the second monitor. This is made possible by the selecting means.

In one advantageous embodiment of the invention, the graphical element is a set of cursors representing potentiometers used to adjust time-gain compensation.

Such a graphical element allows particularly easy, user-friendly monitoring of changes in gain compensation, since the effects of such processing operation are directly added to the duplicate image such as displayed on the second monitor, and hence underneath the potentiometers themselves when the graphical element is superimposed. This allows the processing to be modulated with great accuracy but also with extreme operating simplicity.

In one advantageous implementation, the cursors of the potentiometers can be positioned by detecting the intersection between a finger pathway on the touch screen with the lines along which each cursor is moved.

This characteristic allows very rapid adjustment of gain compensation since only one finger movement is required.

In one advantageous implementation of the invention, the display of the graphical elements on the duplicate ultrasound image is adapted to the needs of image processing in relation to data on the acquisition conditions of the image provided by the ultrasound imaging apparatus and/or the image processing means.

With this characteristic, it becomes possible to modify the number of potentiometers for adjustment of gain compensation, depending on the depth of analysis scanned when acquiring the image.

According to one advantageous characteristic of the invention, the second touch-screen monitor, through touch action on the duplicated image, allows at least one function to be performed from among the functions of zooming, selection of region, size measurement.

Such functions allow zooming in on the image, then selecting a region to which particular processing is to be applied, this processing then being reproduced on the corresponding selected region in the whole ultrasound image such as displayed on the first monitor.

In the selected region, it is generally helpful, with the aid of the touch screen, to be able to take measurements of a structure that is visible in the ultrasound image. This function is generally offered by means of a mouse in known electronic display systems. The use of the touch screen directly on a duplicate of the ultrasound image, or part thereof, allows the utilization of this function with user-friendly means that are very simple to implement.

According to one particular characteristic of the invention, the second touch-screen monitor is capable of being used as write insertion means onto the ultrasound image displayed on the first monitor, or onto a form displayed on the first monitor, the touch screen then displaying a keyboard and write monitoring window, and the application means are able to apply the written text to the ultrasound image such as displayed on the first monitor.

Write insertion is a function also known in the prior art and achieved by means of a keyboard connected to the single monitor used for display. Writing is then directly reproduced on the screen of said single monitor, generally compelling the user to lift eyes from the keyboard to see what has been written on the screen, which is inconvenient for many persons little accustomed to using a keyboard. In parallel, the use of a physical keyboard, which offers comfortable haptic perception, brings major mechanical and ergonomic constraints: space taken up on the control panel or complex mechanical integration.

By proposing the display of a virtual keyboard on the touch-screen monitor, the user has no return of what has been written. Therefore, by providing this virtual keyboard with a write monitoring window, users are able to see what they have written close to the point where their fingers are positioned without having to look up. In this way, any mistakes can be immediately corrected and the writing inserted in the ultrasound image is more practical and reliable.

Additionally, the invention enables savings in space and ease of use compared with the utilization of a mechanical keyboard.

Advantageously, the application means can apply the writing onto the ultrasound image instantly or after each new line.

According to one advantageous characteristic of the invention, the electronic system of the invention comprises body part identification means enabling a body part marker to be displayed on the second monitor symbolising a structure such as imaged in the ultrasound image and to place a probe locating marker identifying its first active element in relation to this body part marker by touching two points on the touch screen or by sliding a finger or stylus on the touch screen from one point to another.

The positioning of such a body part identification marker is generally very complicated in known electronic display systems. The use of the touch screen facilitates the positioning of such a body marker by proposing the display of a symbol representing the body part displayed in the ultrasound image, and positioning of the body location marker by applying the finger to two points or by sliding the finger from one point to another on the touch screen.

This characteristic is particularly advantageous since it allows extensive use of time identification markers, which is currently not the case due to the complex implementation of these markers.

One advantageous characteristic of the invention consists in the fact that the application means are such that an image selected from among others on the second monitor is automatically displayed on the first monitor.

This makes it possible to change the image displayed in large format on the first monitor from among a plurality of duplicate images displayed on the second monitor. Therefore the selection of an image from among several images can be made in a fully user-friendly manner.

According to one useful characteristic of the invention, the second monitor is able to display three-dimensional volumes obtained from at least one ultrasound image displayed on the first monitor and three-dimensional movement means allowing these three-dimensional volumes to be manipulated using the tactility of the second monitor.

This characteristic allows very easy manipulation of three-dimensional volumes, even though the two-dimensional images from which they are generated still remain displayed in large format on the main monitor. The touch-screen is also particularly well adapted to the manipulating of volumes in space using most ergonomic, natural hand movements.

The invention also concerns a method to process an ultrasound image displayed on a first monitor of an electronic display system coupled to ultrasound imaging equipment capable of capturing said image and also comprising image processing means, consisting of the steps of:

duplicating the ultrasound image displayed on the first monitor, and sending this duplicate towards a touch-screen monitor separate from the first monitor, displaying at least part of the duplicate on the touch-screen, displaying on the touch-screen at least one graphical element used to perform at least one processing operation on the duplicated image using the tactility of the screen, performing processing such as controlled via the intermediary of a graphical element, immediate implementation of all processing operations, performed by means of the second monitor, on the duplicate ultrasound image displayed on the second monitor, and immediate or deferred application, to the ultrasound image displayed on the first monitor, of all or part of the processing operations performed on the duplicate ultrasound image by means of the second monitor.

According to one preferred implementation, the different steps of the method are determined by computer programme instructions.

Therefore, the invention also concerns a computer programme product on a data storage medium, this programme being able to be implemented in an electronic display system according to the invention, and this programme comprising instructions adapted for implementation of the steps of the method.

This programme can use any programming language and can be in the form of a source code, object code, or intermediate code between source code and object code such as in a partly compiled form, or in any other desirable form.

The invention also concerns a data storage medium, which can be read by an electronic display system and comprises computer programme instructions such as above-mentioned.

The data storage medium may be any entity or device able to store the programme, for example the medium may comprise a storage means such as a ROM, e.g. a CD-ROM or a micro-electronic circuit ROM, or even a magnetic storage medium, e.g. a floppy disk or hard disk. The medium may also be a USB key or any other memory, notably a so-called flash memory able to contain a computer programme in software form.

Additionally, the data storage medium may be a transmissible medium such as an electrical or optical signal which can be conveyed via an electrical or optical cable, by radio or by other means. The programme of the invention may, in particular, be downloaded from a network of Internet type.

Alternatively, the data storage medium may be an integrated circuit in which the programme is incorporated, the circuit being adapted to run or to be used in running the method under consideration.

BRIEF DESCRIPTION OF THE DRAWINGS

Other characteristics and advantages of the present invention will arise from the description given below, with reference to the appended drawings illustrating an exemplary embodiment thereof which is in no way limiting. In the figures.

DETAILED DESCRIPTION OF ONE EMBODIMENT

Figure 1:
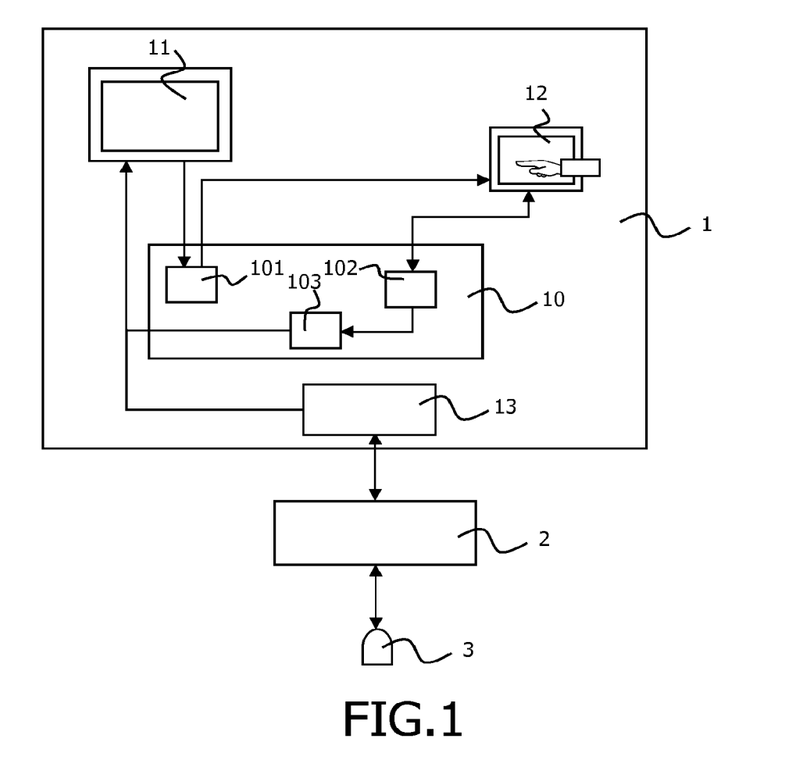
FIG. 1 is a schematic illustration of an electronic display system according to the invention.

FIG. 1 schematically illustrates an electronic display system 1 according to the invention. This electronic display system 1 is coupled to ultrasound imaging equipment 2 capable of capturing an image of a medium using a probe 3.

According to the invention, the electronic display system 1 comprises at least one processing module 10 and two display monitors 11 and 12 of which one, display unit 12, is a touch-screen. The touch-screen 12 can be a single or multi-touch screen.

The processing module 10 comprises at least one sub-module for duplication 101 of the ultrasound image such as acquired using the ultrasound imaging equipment 2 and displayed on the first monitor 11. These duplication 101 means send the duplicate to the second touch-screen monitor 12 on which it is displayed at least in part.

Such a duplicate is obtained using known means, for example partial display of a previous screen capture on the main monitor, or by saving and recopying in a buffer memory comprising the image of the main monitor in another buffer memory containing the image displayed on the secondary monitor. It may also be considered to redirect or share a video flow, via a graphics card, to the two monitors.

Figure 2:
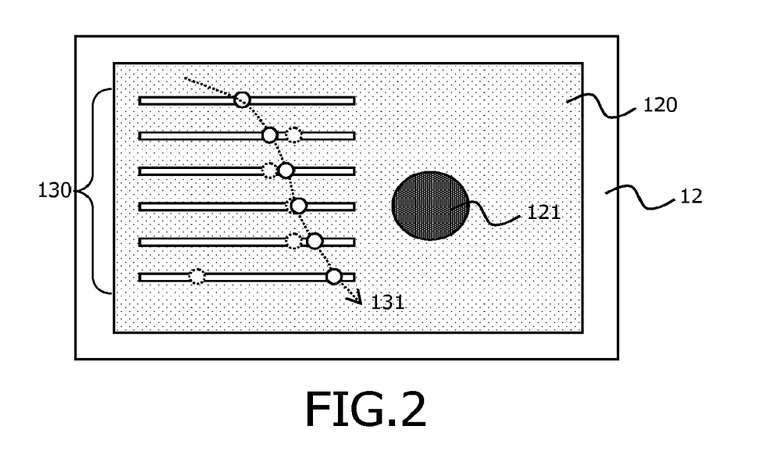
FIG. 2 is a diagram illustrating display of the duplicate image on the second touch-screen monitor, and the display of a graphical element according to one advantageous embodiment of the invention.

FIG. 2 shows an exemplary embodiment of the invention illustrating the touch-screen monitor 12 on which the duplicate image 120 is displayed in the screen background, while slide potentiometers 130 are superimposed over the duplicate image 120. In one advantageous embodiment, the slide potentiometers 130 are used for time-gain compensation, this compensation corresponding to amplification of the ultrasound signal amplitude.

Other applications for use of superimposed potentiometers concern a configuration specifically designed for cardiology. In this case, an additional set of potentiometers can be manipulated vertically on the control panel of the touch-screen.

In the prior art, this compensation is generally installed on a control panel of the electronic display system and uses a fixed number of physical slide potentiometers whose maximum translation distance is therefore also fixed. In this case, it is not possible to modify the number of potentiometers and their range of action in relation to the probe used and/or to the chosen clinical application.

Known implementations are therefore limited. This is a particular hindrance when high-frequency probes are used or when investigation is of shallow depth.

The invention effectively has the advantage of allowing the number of potentiometers to be easily modified, by merely modifying the software so as to display the desired number of potentiometers superimposed over the image 120 of the touch-screen monitor 12.

It is also possible only to display the necessary potentiometers. For example, when the potentiometers are mounted vertically to correspond to strips of successive depths, if the image obtained lies at a shallow investigation depth, it is possible not to display the potentiometers corresponding to the deepest areas. This avoids the neutralizing of potentiometers, which tends to perturb users who often do not realize that the last potentiometers are not being used.

The invention also avoids having to redistribute gain amplifications along the exploration depth over a given fixed number of potentiometers when the user reduces the investigation depth of the image, if two choices of image processing are possible. Such redistribution over a fixed number of potentiometers is a hindrance since it causes variations in the general gain over the whole image when moving through transitions between different depths and incoherency between the mechanical position of these potentiometers and the gain values used. Additionally, if automatic gain compensation is used, there is incoherency between the mechanical position of these potentiometers and the gain values used by the system.

The invention enables all these problems to be solved by allowing the graphical elements, for example the gain compensation potentiometers, to be displayed in the duplicate ultrasound image in a manner fully adapted to the needs of image processing in relation to data on the image acquisition conditions.

In one advantageous embodiment of the invention, the positions of the slides along the potentiometer lines are determined by the intersections between the pathway 131 of a finger on the touch-screen 12 with each line of the potentiometers.

This radically simplifies adjustment of the potentiometers since this allows all the potentiometers 130 to be adjusted in one movement, contrary to general practice as defined in documents describing the implementation of time-gain compensation on a touch screen, namely the individual manipulation of each potentiometer in horizontal translation. This is only possible with a touch screen.

The above avoids the user having to manipulate all the physical potentiometers available on the control panel, either using the palm or the back of the hand, or individually between two fingers.

The attenuation of acoustic waves in a propagation medium in relation to depth is therefore rapidly compensated by means of the correction curve thus determined.

It is nonetheless possible to make provision for each potentiometer to be adjusted by individual horizontal or vertical translation of each slide, performed virtually on the touch-screen 12. Also, if a multi-touch screen 12 is used, the user is able to make parallel translations of several linear potentiometers.

The touch-screen monitor 12 is connected to an image processing sub-module 102 of the processing module 10, so that the processing performed by means of the touch-screen monitor 12 can be applied instantly to the duplicate image 120.

It is noted here that it is most advantageous, by means of the invention, to have the duplicate ultrasound image 120 displayed in the background under the graphical display of the potentiometers 130 so that the effect of translation(s) of the potentiometer slides can be immediately observed.

This effect is visible without the user having to lift eyes from the control elements towards a single display monitor, as is the currently the case with known display systems.

The processing module 10 advantageously comprises a sub-module 103 for application of processing, enabling a choice to be made between immediate or deferred application of the processing carried out on the duplicate image 120, and allowing part or all of these processing operations to be chosen.

The processing operations of the ultrasound image that are chosen by means of the sub-module 103 are applied directly to the ultrasound image displayed on the first display monitor 11.

By means of the two monitors used according to the invention, the user maintains the benefit of analyzing the ultrasound image in its entirety at any time and with the best adjustments on the first monitor 11 on which it is displayed in its greatest size and best resolution. The user may also adjust the image processing operations on the second monitor 12 before transferring the processing operations to the whole image.

The use of the touch-screen 12 in the electronic display system 1 also makes it possible to zoom in on a particular region of the duplicate image, directly through specific finger action on the touch-screen monitor 12. For example, a magnifying zoom can be associated with the spreading of two fingers on the touch-screen 12, and image shrinking with the drawing together of two fingers initially set apart on the touch-screen 12. Such functions are well known in touch-screen technology and will not be detailed further herein.

However, the use of two spread fingers to create the zoom window is only possible with a multi-touch screen.

Therefore, it is possible to achieve this function by means of a rotary wheel commonly called an "encoder", on the touch-screen 12, this wheel being used to zoom in on the image from its centre, choosing from among different zoom factors.

In this way, adjustment of compensation can be achieved in a region of reduced size as defined using the zoom function. Fine-tuned, local compensation adjustments can therefore be easily achieved with the invention.

It is to be noted that, when zooming in on the image on the touch-screen monitor 12, the image on the main monitor 11 is not zoomed, making it possible to assess all the details useful for diagnosis on this main monitor 11 and at the same time to observe contrasts of a lesion on the touch-screen 12 for more fine-tuned analysis subsequent to gain adjustments.

These adjustments may or may not be carried over to the image such as displayed on the main monitor 11.

In one advantageous implementation, to facilitate perception of the duplicated ultrasound image 120 on the touch-screen 12 when the graphical potentiometers 130 are not touched, these potentiometers are made practically transparent. On the other hand, they become opaque as soon as one thereof is touched to achieve better adjustment.

Figure 3:
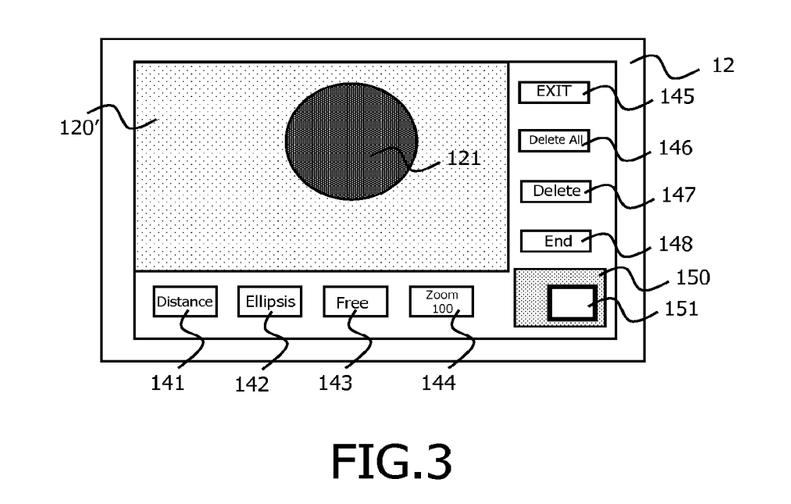
FIG. 3 shows another example of the display of the duplicated image in another embodiment of the invention.

FIG. 3 illustrates a particular screen display in which the duplicate ultrasound image 120 has been zoomed onto a region 120' containing an anomaly 121.

Provision is made so that region 120', defining a zoom window, is able to be moved. Such a moving can be obtained using vertical and/or horizontal scroll bars displayed on the edges of the zoomed image. Instead of scroll bars, it is also possible to use a finger directly applied to the screen which is moved to translate the zoom window in the desired direction in a manner known to those skilled in the art.

As shown in FIG. 3, it is judicious, according to the invention to identify movement of the zoom window using a thumbnail 150 representing the whole ultrasound image with a frame 151 representing the zoom window able to be moved in relation to movement of the zoomed region 120'.

To move the zoom window, provision may be made either to click with a finger on the position corresponding to the desired new position of the zoom window, or to slide the frame 151 representing the zoom window to a new position using the finger.

Once the zoom window 151 is correctly positioned on the region of interest, the zoomed region 120' is advantageously used to take very accurate measurements, of the anomaly 121 in particular, or to determine the shape of the anomaly 121. Measurement of a lesion or anomaly 121 can be made very rapidly and precisely using a finger or a stylus directly applied to the image displayed on the touch-screen and using a certain number of measurement functions proposed by the invention. Conventionally the measurement tools used, mouse or trackball, are distanced away from the monitor. This requires very good coordination of movement. It is detrimental to ease of use and accuracy of measurement, such as when measuring the perimeter of a lesion for example.

In particular, keys can be drawn on the touch-screen 12. These keys, whether or not superimposed, when activated allow a geometric element to be drawn on the zoomed figure 120' and hence allow measurements to be made.

In the example in FIG. 3, the key 141 is a key used to measure a distance between two points by tracing a line between two points, key 142 is a key used to draw an ellipse which will serve to measure a surface, perimeter, length of short axis or long axis, key 143 is a key allowing the freehand drawing of a contour around the anomaly 121 for example, and 144 is a window in which the zoom power is displayed.

A certain number of other buttons/keys provide the possibility of: exiting this display window, button 145; deleting the geometric elements such as drawn in their entirety, button 146, or individually, button 147; freezing measurements, button 148; and freezing the geometric elements drawn on the duplicate image 120'.

At the same time as the different measurements and geometric elements are fixed, they are directly reproduced in real time or by activation of this key 148 onto the image such as displayed on monitor 11.

With these functions of the invention it is very easy to take measurements of circumferences and surfaces drawn freehand. This is particularly useful to characterize the contours and size of a lesion or anomaly 121.

For example, to trace a line measuring a perimeter, the finger is positioned on a point of origin on the touch-screen 12, then the contour of the anomaly 121 is followed with the finger or a stylus. This measurement is then completed by releasing the finger or stylus or by pressing on a dedicated selection key accepting the measurement.

According to the invention, it is contemplated to display the measurement cursors and the trace-line in progress simultaneously on the touch-screen monitor 12 and on the main monitor 11. In this way, it is possible to maintain a conventional measurement approach on the main monitor 11 whilst offering the possibility of taking a highly accurate measurement by working on the smaller touch-screen 12.

The use of the touch-screen monitor 12 allows implementation of other advantageous characteristics which use the tactility of monitor 12 and the transfer of controls onto this monitor.

Figure 4A:
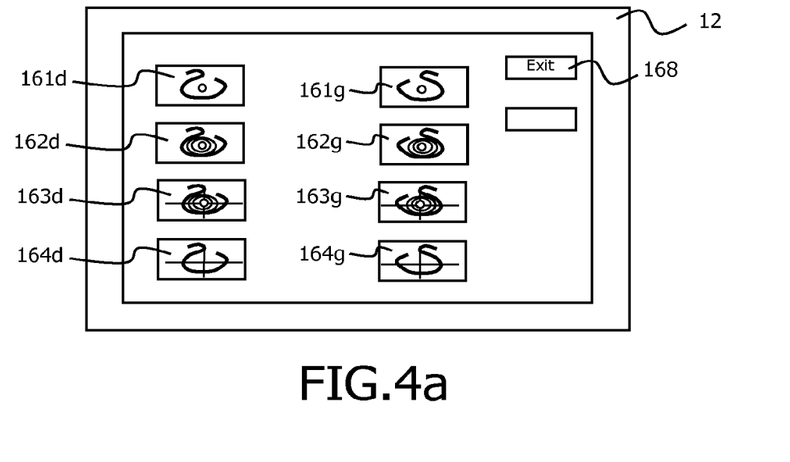
FIGS. 4a and 4b illustrate two more displays on the second touch-screen monitor, according to one advantageous characteristic of the invention, making it possible to position a time identification marker on a symbol of the imaged body part.
Figure 4B:
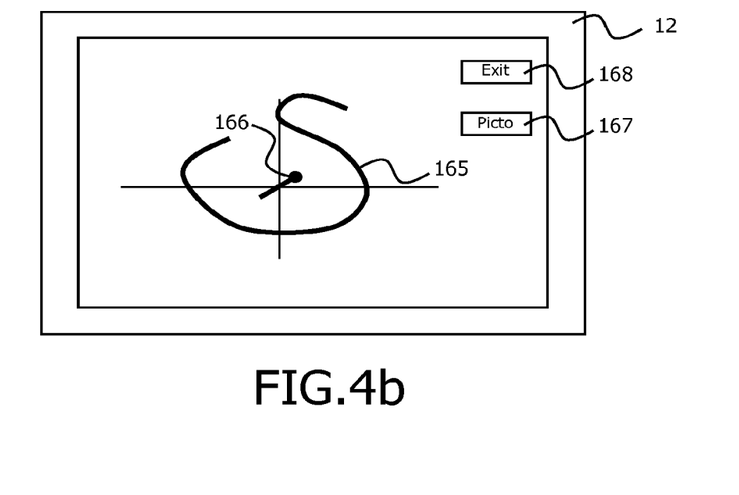

FIG. 4 shows one of these characteristics which allows a probe marker to be positioned with respect to a body location marker.

As illustrated in FIG. 4a, according to the invention, a plurality of buttons allows a choice to be made, directly on the touch screen 12, between different types of body location points all adapted to the imaged organ, in this case a breast. In the example shown in FIG. 4a, the body location points concern the breast. Buttons 161d to 164d offer different body location points for a right breast and buttons 161g to 164g offer different body location points for a left breast.

Once selected, the body location point denoted 165 in FIG. 4b and depicting the chosen left breast, is then displayed full screen as shown FIG. 4b.

A probe marker 166 can then be very easily positioned, on the touch screen 12, by sliding a finger from one end to the other of the point at which the probe was positioned during the examination in progress relative to the body location point 165, or by point-pressing on the two ends of the place where the probe was positioned relative to the body location point 165.

The probe marker 166 is then depicted on the touch-screen 12 by a straight line segment. An additional graph, for example in the form of a semi-circle or circle, appears at the point of first contact on the touch-screen 12 to indicate the position of the first acoustic element of the probe. For the very first selection of a body location point, this point is automatically displayed on the monitor 11.

It is possible to send or not to send the probe marker accompanied by the body location point for printing on the ultrasound image such as displayed, by activating a "display" or "mask" key which allows choice of display or non-display of the body location point on the monitor 11. Key 167 is used to return to the display such as shown FIG. 4a, so that it is possible to choose another body location point. Key 168 is used to exit this function.

This characteristic avoids the application of the positioning means of a marker to a known body location point. Conventionally, selection of the body location point is made via a button on the control panel. On this button a set of location points is shown from which the desired point is to be chosen. Once it is chosen, this location point is displayed on the main monitor and a second action consists of positioning a probe marker on the body location point.

Such action is not easy to carry out since the probe marker must be positioned at the corresponding place on the body location point 165, then this probe marker must be oriented by rotation. This entails a translation movement followed by a rotational movement which compels the user to actuate different controls. It is easy to understand the interest of the invention, which proposes positioning a probe marker in very simple manner.

Figure 5:
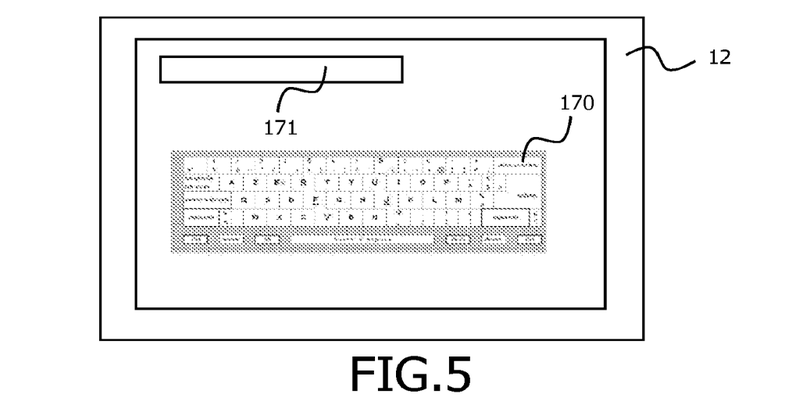
FIG. 5 illustrates the display on the second touch-screen monitor according to one particular characteristic of the invention.

FIG. 5 shows a second advantageous characteristic which can be easily implemented by means of the invention. This characteristic avoids the use of physical alphanumerical keyboards to enter patient data and image annotations, as is the case with all current ultrasound equipment. Their major drawback is to make control panels very cumbersome, even though use of the keyboard is infrequent.

To solve this problem of use of space, it is known to use virtual keyboards graphically represented on the single display monitor used in known viewing systems. This is not practical however, since it reduces available space for the ultrasound image, and at the same time does not provide optimal positioning of these controls for the user who is compelled to lean towards the monitor.

The invention, in addition to the functions particular to the invention concerning superimposed display, allows use of the touch-screen monitor 12 to display a virtual keyboard, limit congestion of the control panel and to make such use of a virtual keyboard more practical. It is ascertained in particular that it is very easy to meet the need for internationalising keyboards, since said virtual keypad can be easily configured in the user's language. It is also found that, unlike the case in which a single monitor or even a touch-screen monitor is used, the touch-screen 12 can be placed at a distance and within ideal reach of the hand of the person using the display system, without hindering the user's view of the main monitor 11.

In FIG. 5, the keyboard 170, represented on the touch-screen 12, is accompanied by a text field 171 positioned on the touch-screen 12 immediately above the keys of the keyboard 170. This avoids the user having to look to and from between the virtual keyboard and the display monitor 11 in which the writing is intended to be inserted.

In practice, the text field 171 is necessarily limited in the number of visible characters, and display is advantageously a scroll display from right to left. This always allows the last characters entered to be seen and checked.

The entirety of the text remains in memory, and therefore any errors can be corrected using conventional forward or back deletion tools or repositioning of the cursor. Advantageously, the field line 171 is emptied of its content when the user moves a cursor onto another text zone in the ultrasound image such as displayed on the main monitor 11, or when pressing a suitable key on the virtual keyboard.

Advantageously when the user positions the text cursor on an area comprising text, this text is displayed in the text field 171 of the keyboard 170. This allows rapid editing of any changes.

It is ascertained that use of a multi-touch screen allows key combinations to be managed on the virtual keyboard 170. For example, a choice can be made between "upper case" and "lower case" using combinations known for conventional keyboards.

Nonetheless, if a single-touch screen is used, the flexibility offered by the virtual keyboard allows lines of special characters to be created that are immediately accessible in the same way as letters of the alphabet, and provision may be made for a specific key to change the whole keyboard from "upper case" to "lower case" and conversely.

Other functions can be implemented by means of the invention through direct use of the touch-screen 12 and independently of image display. This is particularly the case when the electronic display system of the invention and/or the ultrasound apparatus connected thereto is equipped with a configurable dictionary of annotations so that images can be annotated by selecting one term from among a plurality of terms.

The invention offers the user the possibility of scrolling through different annotations in the dictionary with a finger or stylus directly on the touch-screen 12, and subsequently to choose those of interest.

The advantage of this solution is to avoid having to navigate among multiple pages, and obtaining much faster access to the desired function.

Additionally, it is possible to make provision for possible re-organization of the dictionary of annotations, by moving each annotation button to the desired position with a finger or stylus.

According to another characteristic, conventional ultrasound equipment offers the display of thumbnails representing archived images for the examination in progress.

This display is generally given on one of the edges of the single monitor and allows the user, by clicking thereon, to select an image for its full screen display, in particular for the purpose of making annotations and/or taking measurements.

Selection of the desired image from among archived images for an examination in progress, using current means, is complicated since its requires scrolling through the thumbnails to find the image of interest and then to select this image. This generally leads to arbitrating between specific means to select this image and a selecting pointer, e.g. a mouse pointer.

If there is a "review" mode, several thumbnails of acquired and memorized images are saved during the examination. They are displayed when this mode is activated and the user often wishes to reorganize them. This operation proves to be difficult and little intuitive with known tools. With the invention, it is possible to switch all the thumbnails representing archived images for the examination in progress on to the touch-screen 12, and to display them in sufficient size so that they can be identified without, however, displaying them all together on the screen.

It is also possible, according to the invention, to make provision for the size of the thumbnails to be controlled by the user using a specific control on the touch screen 12, for example by magnifying one of the thumbnails with two fingers on a multi-touch screen, the other thumbnails then automatically assuming the same size.

To view those thumbnails which do not appear or which appear only in part on the screen, they can be moved using a finger on a scroll bar.

Then a double-click or double-strike with the finger or stylus on the touch-screen 12 displays the thumbnail full screen on the first monitor 11.

For reorganization of images, use of the touch-screen 12 simplifies the user's task. Using a finger or stylus, the user selects an image and causes it to slide from right to left or from top to bottom. When releasing pressure of the finger the image inserts itself at the point thus defined and the others automatically shift position.

If a thumbnail is moved towards one of the edges of the screen and there are other non-visible thumbnails, these are then automatically moved by the system for display on the touch-screen 12, thereby allowing the insertion of the selected thumbnail at the chosen point.

The invention also allows easy manipulation of three-dimensional volumes or manipulation of associated section planes about three axes of rotation.

These adjustments based on potentiometers, generally one per axis of rotation, are currently possible on conventional ultrasound equipment.

The invention can meet the needs of translating volumes or section planes within the display plane. With the invention it is possible to have a touch-screen 12 that is independent with respect to the ultrasound image display monitor 11, and that permits transferral of three-dimensional volumes or associated section planes.

Once these volumes or section planes have been duplicated on the touch-screen 12, positioning of a finger or stylus in the centre of the volume or section plane commands translation in the plane of the screen 12 and in the direction of movement of the finger or stylus.

Rotations of the volume, in the plane of the screen 12, are made by positioning the finger or stylus on one of the edges of the image and by moving this finger or stylus parallel to one of the edges of the screen.

Rotation about the axis perpendicular to the plane of the screen 12 can be made by choosing one of the following means: positioning the finger or stylus on the circumference of the object and circular movement of this finger or stylus roughly following the periphery of this object, or use of a rotary knob on the touch-screen 12.

It is also possible to use a zoom function on the volume, followed by a "fly through", i.e. visualisation through this zoomed volume.

This zoom function, followed by a fly-through can be achieved using a rotary knob increasing the zoom factor and permitting a fly-through by turning in the knob clockwise. On the contrary, the zoom factor can be decreased and the volume distanced away from the user by rotating the knob anti-clockwise.

It is also possible, if the touch-screen 12 is a multi-touch screen, to position two fingers close centre of the volume and to draw these fingers apart or close to each other depending on the desired zoom effect.

Finally, it is noted that various embodiments can be carried out along the principles of the invention as defined in the following claims.

What is claimed is:

1. An electronic display system for coupling with an ultrasound imaging equipment capable of capturing an image of a medium by means of an ultrasound probe, the system comprising:
    a first monitor to display an ultrasound image captured via the ultrasound imaging equipment;
    a second monitor, separate from the first monitor, the second monitor comprising a touch-screen monitor, the second monitor displaying at least a part of the ultrasound image displayed on the first monitor;
    means for displaying at least one graphical element on the touch-screen monitor, wherein the at least one graphical element is displayed in a superimposed manner over the ultrasound image and wherein the at least one graphical element relates to a processing operation to be performed on an ultrasound image when the at least one graphical element is manipulated by a user in a tactile manner via the touch screen;
    means for processing tactile screen inputs on the at least one graphical element,
    means for allowing size measurement to be performed simultaneously on said first monitor and said touch-screen monitor during simultaneous display of said ultrasound image on said first monitor and at least said part of said ultrasound image on said second monitor; and
    means for:
    instantly displaying the image on the second monitor with said size measurement, such that the user can immediately observe the size measurement on the image on the second monitor based upon said tactile screen inputs, and displaying the ultrasound image on the first monitor with said size measurement caused by the performance of the tactile screen inputs.

2. The electronic system according to claim 1 wherein the system displays measurement cursors and a trace-line in progress simultaneously on the duplicate ultrasound image on the touch screen and the ultrasound image displayed on the first monitor.

3. The electronic display system according to claim 1, wherein the system permits the implementation of a plurality of slide potentiometers, each having a slider, displayed in a superimposed manner over the duplicate ultrasound image and each of whose slider positions are determined by intersections between a pathway of a user finger or user stylus movement on said touch screen with each line of said plurality of slide potentiometers.

4. The electronic system according to claim 3, wherein one of said plurality of slide potentiometers comprises means for adjusting time-gain compensation.

5. The electronic system according to claim 1, wherein size measurement is applied to the ultrasound image displayed on the first monitor is only applied to at least one region selected through touch action on the duplicate ultrasound image using the touch-screen monitor in the duplicate ultrasound image.

6. The electronic system according to claim 1, wherein the touch-screen monitor is able to be used as write insertion means in the ultrasound image or in a text field displayed on the first monitor, the touch-screen monitor then displaying a keyboard and a write display window, and wherein the writing is applied to the ultrasound image or in a text field displayed on the first monitor.

7. The electronic system according to claim 1, wherein the system further comprises body location means, the body location means allowing the display, on the touch-screen monitor, to include a body mark symbolizing a structure as imaged on the ultrasound image, and allowing positioning of a probe body location marker relative to the body mark by touching two points on the touch-screen monitor or by a sliding movement thereupon between two points.

8. The electronic system according to claim 1, wherein the touch-screen monitor is able to display a plurality of miniature images and wherein one of said miniature images chosen from among several on the touch-screen monitor is automatically displayed on the first monitor.

9. The electronic system according to claim 1, wherein the touch-screen monitor is able to display three-dimensional volumes obtained from at least one ultrasound image displayed on the first monitor, and wherein the touch-screen monitor further comprises three-dimensional movement means allowing manipulation of the three-dimensional volumes by means of the tactility of the touch-screen monitor.

10. An electronic display according to claim 1, wherein size measurement includes display of a trace line associated with the size measurement which is displayed simultaneously on the first monitor and the second monitor.

11. An electronic display according to claim 1, further comprising means for providing a modification to said image displayed on the second monitor, and for then transferring said image with said modification to said first monitor.

12. A method for processing an ultrasound image, the method comprising:
    displaying the ultrasound image on a first monitor of an electronic display system, sending the ultrasonic image to a touch-screen monitor of a second monitor independent of the first monitor, and displaying at least part of the ultrasonic image on the touch-screen monitor;
    displaying on the touch-screen monitor at least one graphical element in a superimposed manner over the ultrasound image, wherein the at least one graphical element relates to a processing operation to be performed on the ultrasound image when the at least one graphical element is selected in a tactile manner on the touch-screen monitor by a user;
    allowing size measurement to be performed on the touch-screen monitor, through touch action on the touch-screen monitor, wherein size measurement are available simultaneously on the first monitor and the touch-screen monitor during simultaneous display of said ultrasound image on said first monitor and at least said part of said ultrasound image on said second monitor; instantly displaying the image on the second monitor with modification caused by performance of the size measurement after the size measurement has been selected by the user in a tactile manner of the at least one graphical element displayed on the touch-screen monitor such that the user can immediately observe the effects on the image based upon said tactile screen inputs, wherein the ultrasound image is displayed on the first monitor with the size measurement caused by the performance of the tactile screen inputs.

13. The method according to claim 12 further comprising the step of displaying measurement cursors and a trace-line in progress simultaneously on the duplicate ultrasound image on the touch screen and the ultrasound image displayed on the first monitor.

14. The method according to claim 12, wherein said step of instantly implementing comprises permitting the implementation of a plurality of slide potentiometers, each having a slider displayed in a superimposed manner over the duplicate ultrasound image and each of whose slider positions are determined by the intersection of a pathway of a user finger or user moved on said touch screen with each line of said plurality of slide potentiometers.

15. The method according to claim 12, wherein said step of instantly implementing comprises performing at least one function, through touch action on the duplicate ultrasound image on said touch screen, chosen from among the functions of zoom, region selection, size measurement.

16. The method according to claim 12, wherein said step of instantly implementing comprises the at least one processing operation, applied to the ultrasound imaged displayed on the first monitor, is only applied to at least one region selected through touch action on the duplicate ultrasound image using the touch-screen monitor in the duplicate ultrasound image.

17. The method according to claim 12, further comprising the step of using the touch screen as write insertion means in the ultrasound image or in a text field displayed on the first monitor, said step of using the touch screen as write insertion means further comprises displaying a keyboard and a write display window, and applying the writing to the ultrasound image or in a text field displayed on the first monitor.

18. The method according to claim 12, further comprising the step of providing body marks on the touch screen monitor, said step of providing body marks comprises allowing the display, on the touch-screen monitor, to include a body mark symbolizing a structure as imaged on the ultrasound image, and allowing positioning of a probe body location marker relative to the body mark by touching two points on the touch-screen monitor or by a sliding movement thereupon between two points.

19. The method according to claim 12, further comprising the step of the touch monitor displaying a plurality of miniature images and automatically displaying on the first monitor a miniature image chosen from among several on the touch-screen monitor.

20. The method according to claim 12, further comprising the step of the touch-screen monitor displaying three-dimensional volumes obtained from at least one ultrasound image displayed on the first monitor, including allowing manipulation of the three-dimensional volumes by means of the tactility of the touch-screen monitor.

21. A method according to claim 12, wherein said image displayed on the second monitor receives a modification, and said image with said modification is then transferred to said first monitor.

* * * * *